(12) United States Patent
Wynn et al.

(10) Patent No.: US 7,345,276 B2
(45) Date of Patent: Mar. 18, 2008

(54) ION MOBILITY SYSTEM COMPRISING TWO IMS CELLS OPERATED AT DIFFERENT POLARITIES

(75) Inventors: Paul Grant Wynn, Broxted (GB); James Andrew Breach, Hertfordshire (GB)

(73) Assignee: Smiths Detection-Watford Limited, London (GB)

( * ) Notice: Subject to any disclaimer, the term of this patent is extended or adjusted under 35 U.S.C. 154(b) by 272 days.

(21) Appl. No.: 10/559,104

(22) PCT Filed: Jun. 8, 2004

(86) PCT No.: PCT/GB2004/002410

§ 371 (c)(1),
(2), (4) Date: Dec. 2, 2005

(87) PCT Pub. No.: WO2005/001464

PCT Pub. Date: Jan. 6, 2005

(65) Prior Publication Data

US 2006/0124848 A1    Jun. 15, 2006

(30) Foreign Application Priority Data

Jun. 25, 2003  (GB)  ................... 0314761.8

(51) Int. Cl.
*H01J 49/40*    (2006.01)

(52) U.S. Cl. ..................................................... 250/287
(58) Field of Classification Search ..................... None
See application file for complete search history.

(56) References Cited

U.S. PATENT DOCUMENTS

| 4,445,038 | A | 4/1984 | Spangler et al. | |
|---|---|---|---|---|
| 6,459,079 | B1 * | 10/2002 | Machlinski et al. | 250/286 |
| 6,765,198 | B2 * | 7/2004 | Jenkins et al. | 250/287 |
| 2003/0006778 | A1 | 1/2003 | Aiki et al. | |

FOREIGN PATENT DOCUMENTS

| EP | 0 316 514 A | 5/1989 |
|---|---|---|
| EP | 0 626 579 A | 11/1994 |
| WO | WO 00/52432 A | 9/2000 |

* cited by examiner

*Primary Examiner*—Jack I. Berman
(74) *Attorney, Agent, or Firm*—Foley & Lardner LLP

(57) ABSTRACT

An ion mobility spectrometer system includes two cells (1) and (2) driven by a drive unit (12) so that the cells operate at opposite polarities and are switched between different polarities either at regular intervals or in response to detection of a substance in one cell. Two reagents are supplied to both cells (1) and (2), one promoting detection of a substance in the positive mode and the other promoting detection of a substance in the negative mode so that there is no need to switch reagents when the polarity changes.

12 Claims, 1 Drawing Sheet

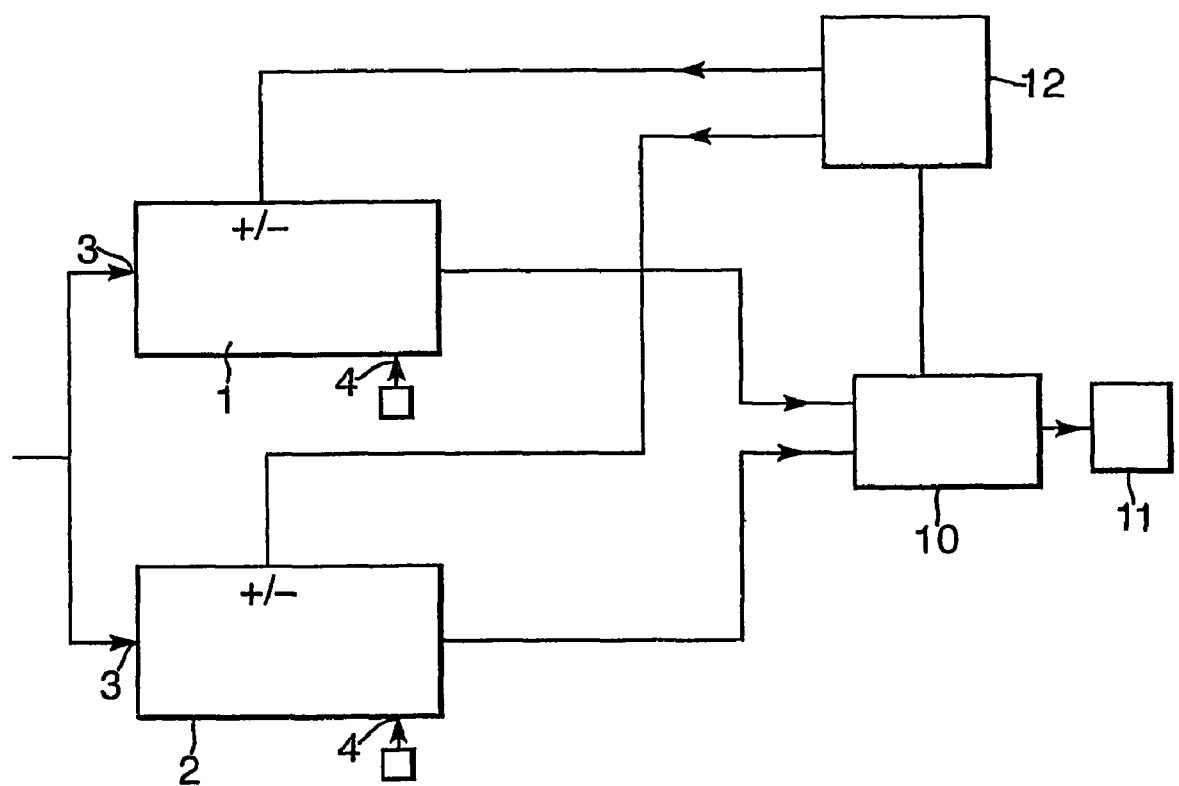

ION MOBILITY SYSTEM COMPRISING TWO IMS CELLS OPERATED AT DIFFERENT POLARITIES

This invention relates to ion mobility spectrometer systems of the kind including a first and second IMS cell, each cell having an inlet by which a vapour or gas to be analysed is supplied to the cells, a driver operable to drive the first and second cells at opposite polarities such that the first and second cells are responsive to respective first and second substances different from one another.

IMS systems are often used to detect substances such as explosives, drugs, blister and nerve agents or the like. An IMS system typically includes a detector cell to which a sample of air containing a suspected substance is supplied as a gas or vapour. The cell operates at atmospheric pressure and contains electrodes energized to produce a voltage gradient across the cell. Molecules in the sample of air are ionized, such as by means of a radioactive source or by corona discharge, and are admitted into the drift region of the cell by an electrostatic gate at one end. The ionized molecules drift to the opposite end of the cell at a speed dependent on the size of the ion. By measuring the time of flight across the cell it is possible to identify the ion. It is common practice to add a reagent or dopant to the cell. The reagent is selected so that it interacts with the substances of interest to produce usually a larger molecule that moves more slowly and can be more readily distinguished from other substances.

Examples of IMS systems are described in GB 2324407, GB 2324875, GB2316490, GB2323165 and U.S. Pat. No. 4,551,624. U.S. Pat. No. 6,459,079 describes a system with a positive and a negative cell, which are each supplied with a different reagent. It is common practice for an IMS unit to have two cells of different polarity since this enables the unit to detect nerve agents, which require a positive polarity cell, and blister agents, which require a negative polarity cell. In such arrangements the positive cell is dedicated to the detection of compounds that produce ionized species in the positive mode, such as nerve agents and narcotics and the negative cell is dedicated to the detection of compounds that produce ionized species in the negative mode, such as blister agents and explosives. Alternatively, some IMS units have only a single cell and the polarity of this is switched between being positive and being negative, the switching period typically being of the order of several seconds. Such an arrangement may be satisfactory in long-term background monitoring but it will be appreciated that the system will not able to respond to certain substances when it is operating at the wrong polarity for these substances.

It is an object of the present invention to provide an alternative IMS system.

According to one aspect of the present invention there is provided an ion mobility spectrometer system of the above-specified kind, characterised in that the driver is operable to switch the polarity of at least the first cell so that it is responsive to a substance different from the first substance.

The driver is preferably operable to switch both the first and second cells so that at any one time one cell is operating at positive polarity and the other is operating at negative polarity. The driver may be operable to switch polarity of the or each cell at regular intervals, preferably less than substantially 30 seconds and preferably less than substantially one second. The driver may be operable to switch polarity in response to a signal indicative of the presence of a substance. The system is preferably arranged to supply reagents to the cells to promote detection of the substances. Both cells are preferably supplied with a first reagent for promoting detection of a substance in the positive mode and a second reagent for promoting detection of a different substance in the negative mode. The system may be arranged to indicate a higher probability of the presence of a substance when it is detected in both cells than when it is detected in only one of the cells. The driver may be operable initially to switch both the first and second cells so that at any one time one cell is operating at positive polarity and the other is operating at negative polarity, and when a cell operating at one polarity indicates the presence of a substance, the driver may maintain that cell at that polarity. When a cell operating at one polarity indicates the presence of a substance, the driver may maintain that cell at that polarity and switch the other cell to the same polarity. The system may include an additional cell operated continuously at one polarity.

An IMS system according to the present invention, will now be described, by way of example, with reference to the accompanying drawing, which shows the system schematically.

The system includes two conventional IMS drift cells 1 and 2 each having an inlet 3 by which gas or vapour to be analysed is supplied to the cells. The cells also have an inlet 4 by which suitable dopants or reagents are supplied to the cells. The internal construction and operation of the cells is conventional so is not described here. The two cells 1 and 2 provide electrical outputs to a signal processor 10, which provides an output to a display, alarm, external communications or other utilisation means 11. The polarity of the two cells 1 and 2 is controlled by a polarity switching or driver unit 12 in the manner described below.

The unit 12 initially applies a positive polarity to the first cell 1 and a negative polarity to the second cell 2. With these polarities, the first cell 1 is responsive to composition A, typically a blister agent, and the second cell 2 is responsive to composition B, typically a nerve agent. Two different reagents are continuously supplied to both cells 1 and 2, namely a first reagent that promotes detection of composition A and a second reagent that promotes detection of composition B. It will be appreciated that the second reagent is redundant in the first cell 1 while it has a positive polarity and that the first reagent is redundant in the second cell 2 while it has a negative polarity. For this reason, multiple dopants may be added to each cell such that each cell has a number of dopants that affect chemistry in the positive mode as well as dopants that affect chemistry in the negative mode.

The unit 12 subsequently switches the polarities applied to the two cells so that the first cell 1 has a negative polarity and the second cell 2 has a positive polarity. With these 4 polarities the first cell 1 is now responsive to composition B and the second cell 2 is now responsive to composition A. Because the cells 1 and 2 are continuously supplied with both the dopants needed to promote detection of the two compositions A and B there is no delay in switching between reagents.

The unit 12 may be arranged to switch polarity of the cells at regular intervals, typically shorter than about 30 seconds. Alternatively, the unit 12 may be arranged to switch polarity only when the inputs to the processor 10 indicate that a composition has been detected by one or other cell 1 or 2. It can be seen, however, that at any time, one cell will be operating at one polarity and the other cell will be operating at an opposite polarity If a suspect composition is detected by one cell and then also by the other cell (having a different dopant chemistry) when its polarity is switched, the processor 10 interprets this as indicating a high probability of the presence of the composition. If, however, a composition is detected by one cell but is not detected by the other cell when the polarity is switched, the processor 10 indicates that there is a lower probability of the presence of the composition. The invention, therefore, by measuring the drift time of ionized species produced in more than one chemistry system, can enable a more reliable assessment of the presence of a substance without undue complexity.

There are various ways in which the system could be modified. For example, the system could have more than two cells, which could be driven with switched polarities or could have a constant polarity. In a system having two cells, there might be situations where it was preferable to have one cell operating continuously at one polarity and to have only the other cell with a switched polarity. Where, for example, it was thought that there was a high risk of a substance that is detected in a positive polarity cell, one cell might be operated continuously with a positive polarity with only the other cell being switched between different polarities. The system could be arranged with both cells initially being driven at different polarities and, when the output of one cell indicates the presence of a suspect composition, that cell could be maintained at its polarity but the polarity of the other cell could be switched to have the same polarity.

The invention claimed is:

1. An ion mobility spectrometer system including a first and second IMS cell, each cell having an inlet by which a vapor or gas to be analyzed is supplied to the cells, a driver that initially drives the first and second cells at opposite polarities such that the first and second cells are responsive to respective first and second substances different from one another, wherein the driver subsequently switches the polarity of at least the first cell so that it is responsive to a substance different from the first substance.

2. A spectrometer system according to claim 1, wherein the driver switches both the first and second cells so that at any one time one cell is operating at positive polarity and the other is operating at negative polarity.

3. A spectrometer system according to claim 1, wherein the driver switches polarity of the or each cell at regular intervals.

4. A spectrometer system according to claim 3, wherein the intervals are less than substantially 30 seconds.

5. A spectrometer system according to claim 4, wherein the intervals are less than substantially one second.

6. A spectrometer system according to claim 1, wherein the driver switches polarity in response to a signal indicative of the presence of a substance.

7. A spectrometer system according to claim 1, wherein the system is arranged to supply reagents to the cells to promote detection of the substances.

8. A spectrometer system according to claim 7, wherein both cells are supplied with a first reagent for promoting detection of a substance in the positive mode and a second reagent for promoting detection of a different substance in the negative mode.

9. A spectrometer system according to claim 1, wherein the system is arranged to indicate a higher probability of the presence of a substance when it is detected in both the cells than when it is detected in only one of the cells.

10. A spectrometer system according to claim 1, wherein the driver initially switches both the first and second cells so that at any one time one cell is operating at positive polarity and the other is operating at negative polarity, and that, when a cell operating at one polarity indicates the presence of a substance, the driver maintains that cell at that polarity.

11. A spectrometer system according to claim 10, wherein when a cell operating at one polarity indicates the presence of a substance, the driver maintains that cell at that polarity and switches the other cell to the same polarity.

12. A spectrometer system according to claim 1, wherein the system includes an additional cell operated continuously at one polarity.

* * * * *